US009486462B2

(12) United States Patent
Montgomery

(10) Patent No.: US 9,486,462 B2
(45) Date of Patent: Nov. 8, 2016

(54) FORMULATIONS OF AMINOGLYCOSIDES AND FOSFOMYCIN IN A COMBINATION HAVING IMPROVED CHEMICAL PROPERTIES

(71) Applicant: CARDEAS PHARMA CORPORATION, Seattle, WA (US)

(72) Inventor: Alan Bruce Montgomery, Medina, WA (US)

(73) Assignee: CARDEAS PHARMA CORPORATION, Seattle, WA (US)

( * ) Notice: Subject to any disclaimer, the term of this patent is extended or adjusted under 35 U.S.C. 154(b) by 0 days.

(21) Appl. No.: 14/469,512

(22) Filed: Aug. 26, 2014

(65) Prior Publication Data
US 2015/0057241 A1 Feb. 26, 2015

Related U.S. Application Data

(60) Provisional application No. 61/870,102, filed on Aug. 26, 2013.

(51) Int. Cl.

| | |
|---|---|
| *A61K 31/665* | (2006.01) |
| *A61K 31/7036* | (2006.01) |
| *A61J 1/20* | (2006.01) |
| *A61J 1/14* | (2006.01) |
| *A61K 9/00* | (2006.01) |

(52) U.S. Cl.

CPC ................ *A61K 31/665* (2013.01); *A61J 1/14* (2013.01); *A61J 1/20* (2013.01); *A61K 9/0078* (2013.01); *A61K 31/7036* (2013.01); *A61J 1/2003* (2015.05)

(58) Field of Classification Search
None
See application file for complete search history.

(56) References Cited

U.S. PATENT DOCUMENTS

| | | | |
|---|---|---|---|
| 2007/0218013 | A1 | 9/2007 | Baker et al. |
| 2011/0124589 | A1 | 5/2011 | Bhatt et al. |
| 2013/0164351 | A1 | 6/2013 | Fernandes |

FOREIGN PATENT DOCUMENTS

| | | |
|---|---|---|
| EP | 2 567 691 A1 | 3/2013 |

OTHER PUBLICATIONS

Dhand et al., "How Best to Deliver Aerosol Medications to Mechanically Ventilated Patients", Clinics in Chest Medicine, 2008, pp. 277-296, vol. 29.
Wood, "Aerosolized antibiotics for treating hospital-acquired and ventilator-associated pneumonia", Expert Review of Anti-infective Therapy, 2011, pp. 993-1000, vol. 1, No. 11.
WO International Search Report, Application No. PCT/US2014/052778, Nov. 10, 2014.

*Primary Examiner* — Layla Berry
(74) *Attorney, Agent, or Firm* — VLP Law Group LLP; Kurt T. Mulville

(57) ABSTRACT

The present invention is synergistic antibiotic compositions having pH adjusted profiles for manufacturing combination, and administration, particularly for patients at risk or suffering from ventilator-associated pneumonia (VAP) and ventilator associated tracheal (VAT) bronchitis. Antibiotic compositions containing fosfomycin and aminoglycosides having individually predetermined and selected pH ranges are manufactured and stored for in combination prior to aerosolization, preferably with a specially designed in-line nebulizer attached to a ventilator.

33 Claims, 2 Drawing Sheets

FORMULATIONS OF AMINOGLYCOSIDES AND FOSFOMYCIN IN A COMBINATION HAVING IMPROVED CHEMICAL PROPERTIES

CROSS REFERENCE TO RELATED APPLICATIONS

This application claims the benefit of U.S. Provisional Application No. 61/870,102 filed Aug. 26, 2013; which application is incorporated herein by reference.

BACKGROUND

A number of justifications exist for formulating two or more antibiotics into a combined formulation, including targeting bacterial infections having more than one organism or type of organism where each requires a different antibiotic to treat the infection. Additionally, drug-resistant bacteria greatly increase the amount of antibiotic required for therapeutic treatment. Combinations of antibiotics with synergistic effects would reduce the overall amount of drug required and increase the effectiveness of the treatment.

Several combinations of antibiotics are in common use and certain combinations are specifically formulated to be inhaled to treat infections of the respiratory tract, including the lungs. Because lung infections are notoriously difficult to treat with oral or intravenous administration of antibiotics, combinations of inhaled antibiotics are particularly valuable. Also, where a lung infection is a combination of Gram-negative and Gram-positive bacteria, antibiotics against each are necessary. Aerosol antibiotic therapy to treat Gram-negative pneumonia in patients on mechanical ventilation has been studied for over 30 years; however, to date no multicenter placebo controlled randomized trial has proven efficacy. There are multiple technical reasons for this, including drug delivery and choice of antibiotic. Additional unique challenges treating bacterial infections in patients on respirators and related solutions to those challenges are described in US 2013/0014759, which is incorporated herein by reference.

One example of an antibiotic combination would include fosfomycin. Fosfomycin is a broad-spectrum antimicrobial with activity against most of the aerobic Gram-positive and Gram-negative bacteria. Fosfomycin is a phosphonic acid derivative, which acts primarily by interfering with bacterial peptidoglycan synthesis, thereby disrupting bacterial cell wall synthesis. Fosfomycin does not undergo metabolism in the body and is primarily excreted unchanged in the urine by glomerular filtration.

Aminoglycosides are a group of bactericidal drugs sharing chemical, antimicrobial, pharmacologic, and toxic characteristics. The group includes streptomycin, neomycin, kanamycin, amikacin, gentamycin, tobramycin, sisomicin, arbekacin, netilmicin, paromomycin, and spectinomycin. Aminoglycosides inhibit protein synthesis in bacteria by inhibiting the protein synthesis function of the bacterial ribosome. All aminoglycosides are potentially ototoxic (damage to the ear) and nephrotoxic (damage to the kidneys). Because of their toxicity and the availability of less toxic antibiotics, aminoglycosides have been used less often in recent years and to treat resistant Gram-negative organisms that are sensitive only to aminoglycosides. Combinations of tobramycin with fosfomycin are described in Baker et al. U.S. Pat. No. 7,943,118.

Amikacin is a synthetic aminoglycoside used to manage infections caused by Gram-negative bacilli resistant to gentamycin and tobramycin. Amikacin is most commonly used on serious Gram-negative infections involving skin and soft tissue, bone and joint, abdominal and urinary tract, and severe respiratory infections. Amikacin's use can include coverage against some aerobic Gram-positive bacteria, which include *E. coli, klebsiella, proteus, pseudomonas, salmonella, enterobacter, serratia* and *mycoplasma*. Like other aminoglycosides, amikacin has a similar potential for ototoxicity and nephrotoxicity especially when given by parenteral administration due to systemic absorption. Amikacin used for intravenous administration is formulated as amikacin-sulfate.

Both fosfomycin and amikacin have been used in the past as inhaled antibiotics. However, each of fosfomycin and amikacin has unique manufacturing and storage characteristics based on their unique chemistry and these characteristics significantly affect their usefulness when combined and used to treat infections in patients. The performance characteristic of each antibiotic, either alone or in combination, can be improved by formulation strategies that improve the storage and safety characteristics of each antibiotic agent. In some cases, common reaction characteristics exist across classes of antibiotics and formulation strategies can be extended from individual species to the broader class of antibiotic. Where formulated for inhalation, other aminoglycosides, such as tobramycin and gentamycin can also be improved by formulation strategies to improve storage and safety characteristics.

Accordingly, a need exists for compositions, manufacturing and storage methods, and systems for combining combinations of fosfomycin and aminoglycosides to maximize the utility of specific antibiotic combination formulations and to enhance their safety.

SUMMARY OF THE INVENTION

The present invention is an improved formulation of aminoglycosides, including tobramycin, gentamycin arbekacin, or anamikacin chloride solution created by dissolving the free base in water with subsequent pH adjustment with HCl) combined with a fosfomycin disodium solution, each produced by synthesis and formulation strategies designed to yield specially selected individual pH values, individual ranges, and differences in pH values and ranges between the two solutions in combination. The individual pH ranges and values offer improved safety for the individual components, and improved chemical properties for the combination, and improved pH values and ranges both individually and in combination.

The antibiotic compositions of the invention include aminoglycosides specially formulated for stability and safety, including amikacin chloride, tobramycin sulfate and gentamycin sulfate or chloride, in a combination composition with fosfomycin solutions. Each component of the composition is individually formulated to be closer to physiologically compatible pH and, when combined, yield a pH-controlled hypertonic combination solution having preselected and defined pH values and ranges that are also physiologically compatible and formulated for aerosolization and inhalation. Accordingly, the invention includes formulations and defined pH values and ranges for each individual component and for the combination. The use of free base of aminoglycosides is preferred as the HCl subsequently used to adjust the pH provides a permeant anion in the solution that is required to prevent cough. If a sulfate salt is used, additional NaCl is needed which would increase the osmolality of the solution.

The invention includes the pH values together with defined molar ratios of the individual components that are chosen for individual stability and compatibility upon formulation into a final combination for administration. Typically, the combined solution will be a two-component mixture that also has selected permeant ion concentrations, designed to be tolerant upon inhalation, including specific chloride ion concentrations, particularly where the permeant ion is contributed by the amikacin chloride component. The formulations offer improved stability during storage and improved safety if either component is given alone. Furthermore, the individual components are formulated to have specific pH values and ranges that are safe because both components are close to physiologic pH. Accordingly, if a medication or hospital error occurs and only one component is delivered to the patient, the adverse effect is minimized. Moreover, because the individual solutions are each pH balanced, the two components can be combined and directly administered to the patient without the need for additional formulation or pH adjustment in the pharmacy or hospital. This is an additional safety feature that eliminates another potential source of error in delivery of the compounds to the patient.

The selected properties of the individual antibiotic components, both individuals upon combination, are suited for delivery as an aerosol mist having a range of particle sizes and osmolality levels designed for treatment or prevention of bacterial infections in the lungs. These physical and chemical parameters are uniquely selected to enhance the bacteriastatic and/or bacteracidal performance of the drug combination in both ventilator-based and nebulizer-based modes of administration.

Specifically, the ratio of the quantity of aminoglycoside to fosfomycin is bactericidal for the target organism and preferably greater than 1:1, greater than approximately 1.5:1.0, greater than or equal to approximately, 9:5, greater than or equal to approximately 2:1, and preferably greater than or equal to approximately 2.5 or 2.6:1.0. In the embodiment of the amikacin chloride solution, the pH is generally between about 6.5-7.5 and the pH range of the fosfomycin solution is generally between about 7.5 and 8.5. Accordingly, the difference between the pH value of the aminoglycoside solution and the pH value of the fosfomycin solution is preferably less than or equal to approximately 2.0, or less than approximately any difference in value among 1.75, 1.5, 1.25, 1.0, 0.75, 0.5 or 0.25. The concentration of permeant ion is greater than 30 equivalents per liter and, in some formulations, greater than 40 milliequivalents per liter. The osmolality is greater than 300-310 mOsm/L and less than about 800 mOsm/L and generally less than 1,000 mOsm/L.

The concentration of the aminoglycoside and the fosfomycin disodium component are, both individually and synergistically in combination, bactericidal, and preferably reach a value of greater than MIC 90 for a target organism or combination of organisms. An aerosol is formed from the combined solution and has osmolality values as described above as tailored by the permeant ion concentration to be tolerated upon aerosol administration. Therefore, the antibiotic components are two individual pH-controlled sterile solutions containing specific amounts and concentrations of each antibiotic compound and formulated in pH values and ranges that are selected for long-term stability during storage. The individual solutions have specially designed storage and reformulation packaging to provide a safe and sterile combination prior to delivery to the nebulizer, and administration to the respiratory tract of a patient. An important safety feature is the limited difference in the individual pH of the two solutions and the balance between the two pH values permits combination of the two solutions and direct administration to a patient without additional pH adjustment. The invention also includes formulation and packaging strategies for each antibiotic component to achieve the selected pH range while maintaining sterility and stability during long-term storage, and to permit re-administration immediately before use without pH adjustment.

Finally, because the safety and synergistic effects of the composition are uniquely suited to treatment or prevention of an infection with a drug-resistant organism, the invention includes testing for drug-resistant organisms, such as multidrug resistant gram negative bacteria and MRSA, and adjusting the combined dose of the antibiotics to treat such an infection, optimally followed by additional testing or treatment to confirm elimination of the infection.

DETAILED DESCRIPTION OF THE INVENTION

Figure 1:
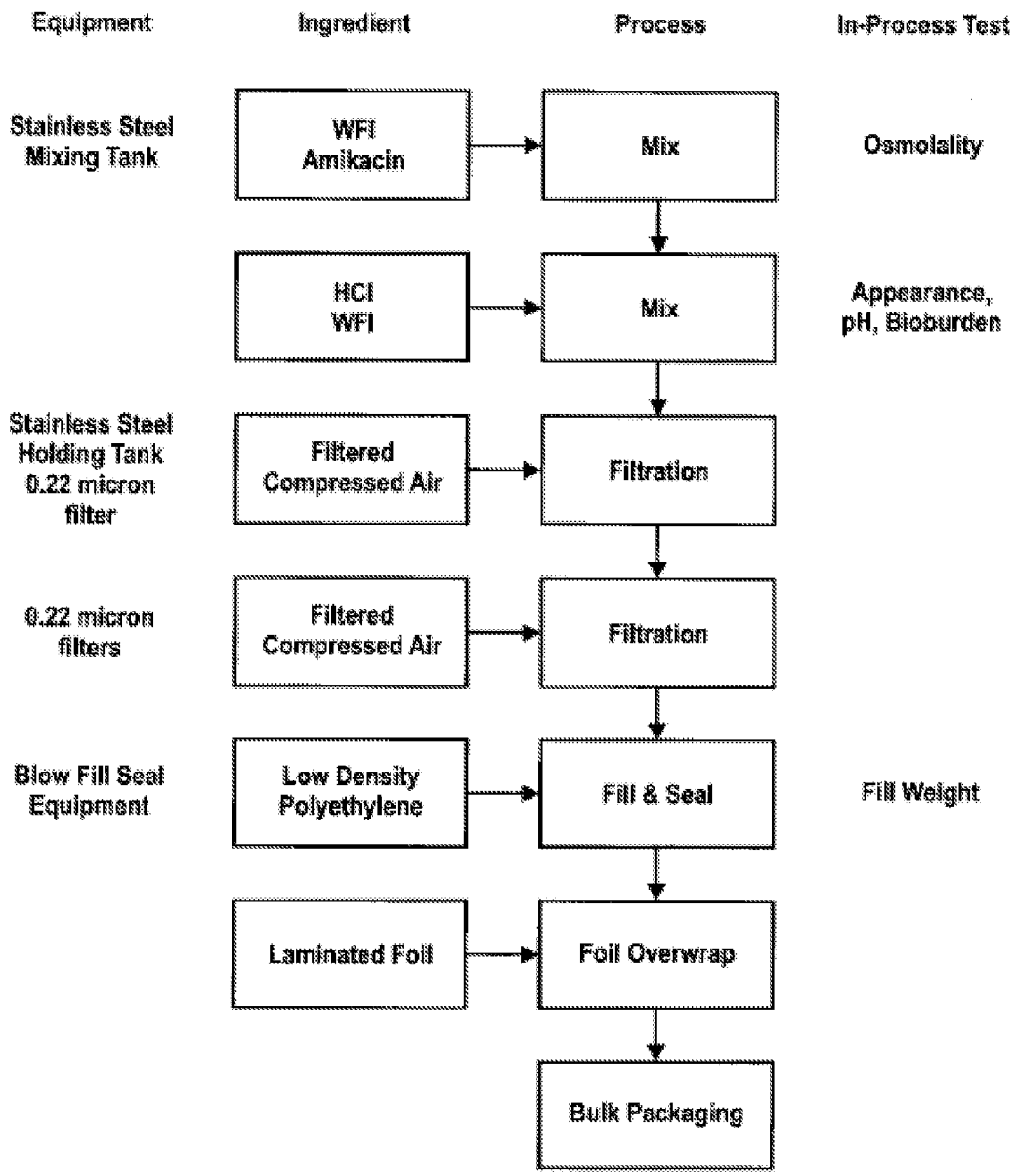
FIG. 1 is a flow diagram of the manufacturing steps of the aminoglycoside solution, specifically the amikacin chloride solution.

A first component is a specially formulated aminoglycoside solution amikacin chloride having a pH between about 6.5 and about 7.5. Although amikacin sulfate is a well-known and widely used aminoglycoside having activity against Gram-negative organisms, amikacin chloride has not been described for aerosol use. The amikacin chloride solution described below uses chloride as the counter-anion both for pH compatibility with the fosfomycin solution and for permanent ion concentration to enhance tolerability and efficacy upon aerosolization. Another aminoglycoside formulated for aerosol delivery is tobramycin sulfate (TOBI®). TOBI has been used in cystic fibrosis patients for many years and is well recognized as the treatment of choice for *pseudomonas aeruginosa* infections. Aminoglycosides have a similar pKa (for example, gentamycin 8.2, amikacin 8.1, arbekacin 10.2, tobramycin has three pKa points of 6.7.8.3 and 9.2) and the manufacturing and formulation approaches described for amikacin could be applied to all aminoglycosides.

A second component is a fosfomycin solution. Fosfomycin is a broad spectrum phosphonic acid antibiotic that has both Gram-positive and Gram-negative activity. However, fosfomycin is subject to an epoxide ring-opening hydrolytic degradation reaction at lower pH. For this reason, fosfomycin is typically formulated at relatively high pH, i.e. between 0.8 and 13. The fosfomycin solution of the present invention is formulated as the disodium salt and has a pH nearer to neutral, typically between 7.5 and 8.5 while maintaining stability for long-term storage. The fosfomycin solution has less than 5% impurities after two years storage and preferably less than 3%. To reduce impurities, particularly the by-products of the epoxide ring hydrolysis, the formulation is manufactured and/or stored at 5° C. or less.

The combined formulation of the aminoglycoside and fosfomycin solutions is a neutral pH hypertonic solution of at least about 50 mg/mL of amikacin with chloride as the counter anion, and at least about 20 mg/mL of fosfomycin with at least 30 milli equil/L of chloride anion. The osmolality of this formulation is approximately 700 milliosm/L with the final chloride concentration of between about 175 and about 275 and preferably approximately 225 milli equiv/L. If the combination is aerosolized and combined with humidified air, the final osmolality is approximately 425 milliosm/L. The permeant anion prevents cough in patients with mild asthma. In the amikacin-chloride embodiment of the permeant ion concentration from the chloride anion and the near physiological pH of the individual solutions avoids the need for the use of additional HCl to pH balance the pH of the combined solutions after reconstitution—a step performed in a hospital pharmacy that introduces the potential for hospital error and may not be available after hours when this medication is intended for seriously ill patients in which prompt treatment is essential.

In clinical use, concentration of the aminoglycoside and fosfomycin are delivered to yield a concentration in the lungs that is MIC90 for the target organism. For amikacin, about 45 mg of amikacin chloride and about 30 mg of fosfomycin disodium are delivered to the lung (50 mg amikacin chloride and 20 mg fosfomycin in solution) using a nebulizer with an expected 15% delivery efficiency. The predicted concentrations of amikacin chloride delivered to the lungs are about 13,500 ug/mL—greater than 25 times the MIC90 for most highly resistant Gram-negative organisms. The predicted peak concentrations of fosfomycin are about 5400 ug/mL—greater than 25 times greater than the MIC90 for *Staphylococcus aureus* based on the similar ratios of deposited drug (in mg) to sputum concentrations. Dosing for aerosolized antibiotics is generally BID (twice daily) or TID (three times daily) because little therapeutic drug remains after 5 half lives or approximately ten hours. Systemic absorption of deposited drug is about 10%, thus, even with sputum concentrations on average 100 fold greater than what can be achieved with intravenous drug, the systemic exposure of aerosol antibiotics is on the order of only 10% of a therapeutic intravenous dose.

In the methods and compositions of the present invention, the combination solutions are provided in 2 separate sterile solutions each having a pH within less than 2.0 units of each other, such that each is at a physiologically tolerable pH. Each antibiotic component of the combination is dissolved in a sterile hypertonic solution as described herein and stored separately, but preferably in a single package. Preferably, the two compositions are combined immediately prior to and administration using a single-use solution package designed to completely combine the packaged contents of each solution to facilitate quantitative delivery of the combined solution to a nebulizer.

For prevention or treatment of ventilator-associated infections, the nebulizer is preferably an in-line nebulizer located within the airway of a mechanical ventilator. Alternatively, the combination may be administered from the drug reservoir of a stand-alone nebulizer. Outside the ventilator setting, the antibiotic combination can be delivered through any ordinary nebulizer for patients suffering from COPD, pneumonia, or asthma. In such circumstances, the total composition of the administered antibiotic, the formulation parameters, and all other characteristics of a bactericidal treatment regimen as described herein are maintained.

To administer the antibiotic combination in a ventilator setting, the in-line nebulizer is connected to the airway of the ventilator distal to the wye and activated to create the aerosol mist. Upon delivery, the nebulizer generates the aerosol mist from a vibrating apparatus disposed therein, typically a vibrating mesh or membrane that has numerous apertures formed therein to produce particles of a defined size from solution. The humidification generator is activated and maintained in operation during each delivery of the aerosol mist formed from the combination solution such that the osmolar load is reduced. The advantage of an in-line nebulizer as described herein is to permit the humidified air in the ventilation airway to pass through the nebulizer and to combine with the aerosolized portion of the hypertonic, pH-balanced antibiotic combination solution.

As delivered, the combination aminoglycoside and fosfomycin solution has a near neutral pH resulting from balancing the quantity, concentration, pH, and formulation of the individual sterile aminoglycoside and fosfomycin components as described in the examples below.

An clinically effective dose of amikacin chloride for the 50 mg/ml amikacin chloride solution and 20 mg/ml fosfomycin solution delivered to the in-line nebulizer. Testing for presence of resistant bacteria could justify reduced dosages because if resistance is not detected, a lower dose will likely be efficacious. The optimally effective dose of fosfomycin is likely at least 15 mg delivered to the lung, with nebulizer doses ranging from 50 to 200 mg depending on nebulizer efficiency. Decreased bacterial density of both *pseudomonas* and *Staphylococcus aureus* in a subset of patients who were co-infected were achieved with approximately 20 mg delivered to the lung (Trapnell et al., supra). In this trial, an estimated 40 mg delivered dose of fosfomycin was more efficacious in killing *staphylococcus* than the estimated 20 mg dose, showing that a higher dose may be better. The most soluble fosfomycin salt is the disodium salt and is preferable although other salts are possible—such as calcium and tromethamine.

A formulation of 10 mL, with 100 to 300 mg fosfomycin and 300 to 600 mg of amikacin at the 15% efficiency rate would provide adequate killing for *Staphylococcus aureus* and *Pseudomonas*. An ideal formulation would contain at least 20 meq/L of chloride anion after dilution. The estimated osmolality of a solution of 50 mg/mL amikacin and 20 mg/mL of fosfomycin, with chloride anion, combined to yield a pH between 6.5 and 8.5 is approximately 750-850 osm/L. If diluted by humidification, this would likely be close to the isotonic range when deposited in the airways. To vary the delivered dose, a smaller or larger volume could be used, or alternatively or in combination, trigger delivery on inspiration phase of breathing to increase the deposition amount.

The recent development of vibrating plate nebulizers, particularly one by PARI, enables particle sizes less than 5 microns. See WO 2005/048982A2. Membranes having a plurality of small apertures therein can produce mean particle sizes less than 5 microns and in the range of 3.5 microns. This is accomplished by making the porous holes smaller during the laser-drilling process. Other vibrating plate membranes by PARI have a 4.5 micron average size particle, as does the vibrating plate nebulizer introduced by Aerogen/Nektar. Similarly, there are small particle jet nebulizers that can produce 2-3 micron size particles. Current ultrasonic nebulizers produce an average particle size of 5 microns using a 2.7 MHtz driving frequency.

As noted above, the present invention includes the use of humidification as a technique to improve the tolerability of hypertonic solutions delivered as an aerosol. The creation of an aerosol with a small particle size from a hypertonic solution can produce a composition of small particles that carry a desirable therapeutic dose but are poorly tolerated due to a high osmolality, i.e., on the order of threefold or greater of normal osmolality, (e.g., ≥930 mOsm/kg). Adding humidification to the aerosol yields an aerosol composition that has a reduced osmolality and is preferably close to isotonic or less than twofold normal osmolality (e.g., <620 mOsm/kg). The humidification is created by an inline humidifier to decrease the osmolality to a range from greater than threefold to less than twofold normal osmolality and may vary depending on the nature of the original hypertonic solution. The particle size of non-humidified aerosol such as the hygroscopic growth of a 4 micron particle may lead to much more dilution than growth of sub 3 micron particle. In such hypertonic solutions, the permanent ion in solution is preferably greater than 40 mequil/L.

In the aspect of the invention below, aminoglycoside/fosfomycin combinations are hypertonic on administration but close to isotonic upon delivery by the advantage of increased humidification compared to ambient air. For instance, if the particle size grows on average from 3.5 to 4.5 microns, the dilution is a function of the cube of the radius or 4.91/11.3. Therefore, the use of small particle aerosol with subsequent hygroscopic growth due to humidification would substantially reduce the osmotic load on the lung. With a larger initial particle size, the effect would be similar. For example, the growth from a 5 to 6 micron particle would lead to a dilution of 15.6/27.

Since the volume of sphere is function of the third power of the radius, the following equation yields the dilution factor:

$$\frac{1.45 \times 1.45 \times 1.45}{1.6 \times 1.6 \times 1.6} = 0.75$$

Thus, the formulation on average is diluted by a factor of 0.75, indicating the formulation has an osmolality of 592×0.75=444 mOsm/Kg.

If particles are allowed to grow much larger than 5 microns, tolerability is not the primary issue, as little will be deposited in the airways due to "rain out" in the ventilator and endotracheal tubing due to the hygroscopic growth. For instance, applying the ratio of 4.91/11.3, if a hypertonic solution is used with a nebulizer that has a 3.5 micron average particle, an osmolality of up to 710 would become, on average, isotonic. Slightly hypertonic formulations can be tolerated by the lung, and it is likely a formulation with an osmolality of up to 800 would be well tolerated by applying the humidification technique described herein.

The PARI in-line nebulizer designed for ventilator use can be outfitted with a small pore membrane, has a current volume capacity of 10 mL, and has a rate of delivery of 0.5-0.6 ml/minute. Although it is currently not configured for triggering on inspiration, a nebulizer may be so configured when operably connected to the control system of the ventilator. Particle size would be estimated at 3.2 microns.

EXAMPLE 1

Amikacin Chloride Formulation from Amikacin-Base and Chloride Counter Anion for pH Balance Amikacin Base, EP is compendial (Ph Eur) and is manufactured by ACS Dobfar S.p.a under DMF 13762. Rather than commercial amikacin sulfate, the amikacin base is the starting material. Amikacin base has a pH of approximately 11, and large amounts of HCl are required to neutralize the pH. In the two-part formulation (used to combine with equal volumes of 40 mg/mL fosfomycin to generate the final formulation of 50 mg/mL amikacin, 20 mg/mL fosfomycin), the amikacin 100 mg/mL solution has a final pH greater than 6 and preferably between pH 6.5-7.5 and has an osmolality of approximately 533 mOsmol/kg, of which only approximately 170 mOsmol/kg is due to the amikacin, the balance is from the chloride anion. This concentration of chloride anion provides the permeant anion that will prevent cough.

The starting pH of commercially available amikacin sulfate is 3.5-5.5 and little or no HCl is needed to neutralize the pH of the solution. As described above, a final formulation has an amikacin concentration of 50 mg/ml and chloride anion concentration of approximately 265 meq/liter. The low end of an acceptable range would be an amikacin concentration of 25 mg/ml and chloride anion concentration of approximately 130 meq/liter; however, as low as 30 meq/liter could be used with another anion in addition to chloride. The high end of the amikacin concentration would be 100 mg/ml and a chloride anion concentration of approximately 540 meq/liter. This formulation yields an osmolality of 900 mOsmol/L, and any increase would prevent dilution of the formulation with humidity sufficient to make it tolerable.

The amikacin chloride solution is stored as a 3 mL sterile unit dose ampoule that is stable at room temperature but is preferably packaged together and stored with the fosfomycin solution at less than 5° C.

The flow diagram depicting the steps of the manufacturing process of amikacin chloride solution is provided in FIG. 1. The flow diagram indicates where each raw material enters the manufacturing process.

The amikacin solution is manufactured as follows:
1. Add the calculated amount of Water for Injection (WFI) to the stainless steel tank.
2. Add the calculated amount of amikacin to the tank and mix until dissolved.
3. Add 90% of the calculated amount of HCl and mix for 5-10 minutes.
4. Titrate the amikacin-HCl solution with remaining HCl until solution reaches pH 7.0±0.3.
5. Bring the solution to final mass with WFI and mix for 10-15 minutes.
6. Filter the solution through a 0.22 micron filter into a holding tank.
7. Filter the solution through two 0.22 micron filters in series.
8. Use Blow/Fill/Seal equipment to form the LDPE ampoule, fill to a target weight and then seal the ampoule.
9. Perform 100% visual inspection and integrity testing on LDPE ampoule.
10. Foil overwrap ampoules individually.
11. Perform 100% leak detection on foil overwrapped ampoules.

EXAMPLE 2

Tobramycin Formulation for pH Balance

Aerosol Aminoglycoside Formulation

Aminoglycosides of the invention are antibiotics, such as gentamycin, amikacin, kanamycin, streptomycin, neomycin, netilmicin and tobramycin.

The aminoglycoside formulation contains from 200-500, preferably 300 mg of aminoglycoside sulfate per 5 ml of the quarter normal saline. This corresponds to 40-100, preferably 60 mg/ml of aminoglycoside, a minimally efficacious amount of aminoglycoside to treat *Pseudomonas aeruginosa* lung and airway infections.

Typically, about three hundred mg of aminoglycoside is dissolved in 5 ml solution of a diluted, typically quarter normal saline containing about 0.225% NaCl.

The tobramycin formulation containing ¼ NS with 60 mg of tobramycin per ml of ¼ NS has an osmolarity in the range of 165-190 Mosm/l. A further advantage of 0.225% NS solution with 60 mg/ml tobramycin is that this formulation is more efficiently nebulized by an ultrasonic nebulizer compared to tobramycin formulated in a solution 0.9% normal saline.

An aerosol with a pH between 5.5 and 7.0 is considered to be safe. Any aerosol having pH greater than 8.0 is to be avoided as the body's tissues are unable to buffer alkaline aerosols and as a result irritation with bronchospasm occurs.

The pH is equally important for stability of the tobramycin solution because degradation occurs at pH greater than 7.0. In the stability studies of 0.225% saline 60 mg/ml tobramycin solution, accelerated stability testing at 40° C. at pH 7.0 showed, at one month, obvious yellowing of the solution indicating the presence of chromophore degradation product. This reaction was less apparent at pH 5.5 or 6.5. At such pH, apparently, the degradation is not present or is much slower. For these reasons as well as for the avoidance of bronchospasm in patients, the optimum pH for the aerosol formulation was determined to be between pH 5.5 to pH 6.5.

The formulated dose of 60 mg/ml of one quarter diluted saline has been found to be optimal for the most efficacious delivery for jet and ultrasonic nebulizers. Although in some instances both lower or higher doses, typically from 40-80 mg/ml may be advantageously used, the 60 mg/ml dose of tobramycin is preferred. A more concentrated tobramycin solution has three disadvantages in a jet or ultrasonic nebulizer. First, if the solution approaches the solubility of tobramycin, 160 mg/ml, precipitation on storage is expected. Second, a higher concentration of tobramycin than is clinically needed is economically disadvantageous. Thirdly, a more concentrated solution will increase the osmolality of the solution, thus decreasing the output of the formulation with both jet and ultrasonic nebulizers. The alternative of a more concentrated solution in a smaller total volume is also disadvantageous.

The dose lower than 60 mg of tobramycin per ml of diluted saline is not sufficient to suppress bacteria, and or treat the infection as there is a wide range of antibiotic sensitivity in bacteria and treating only the susceptible bacteria would lead to the selection of highly resistant strains. Lower concentrations of tobramycin will not be sufficiently effective in at least 90% of patients.

EXAMPLE 3

Fosfomycin Formulation for pH Balance

Fosfomycin Disodium is compendial (Ph Eur) and is manufactured by Ercros, S.A. under DMF 14341. The API is manufactured in Madrid, Spain.

Fosfomycin solution is stored as a 3 mL sterile unit dose ampoule (40 mg/mL).

Figure 2:
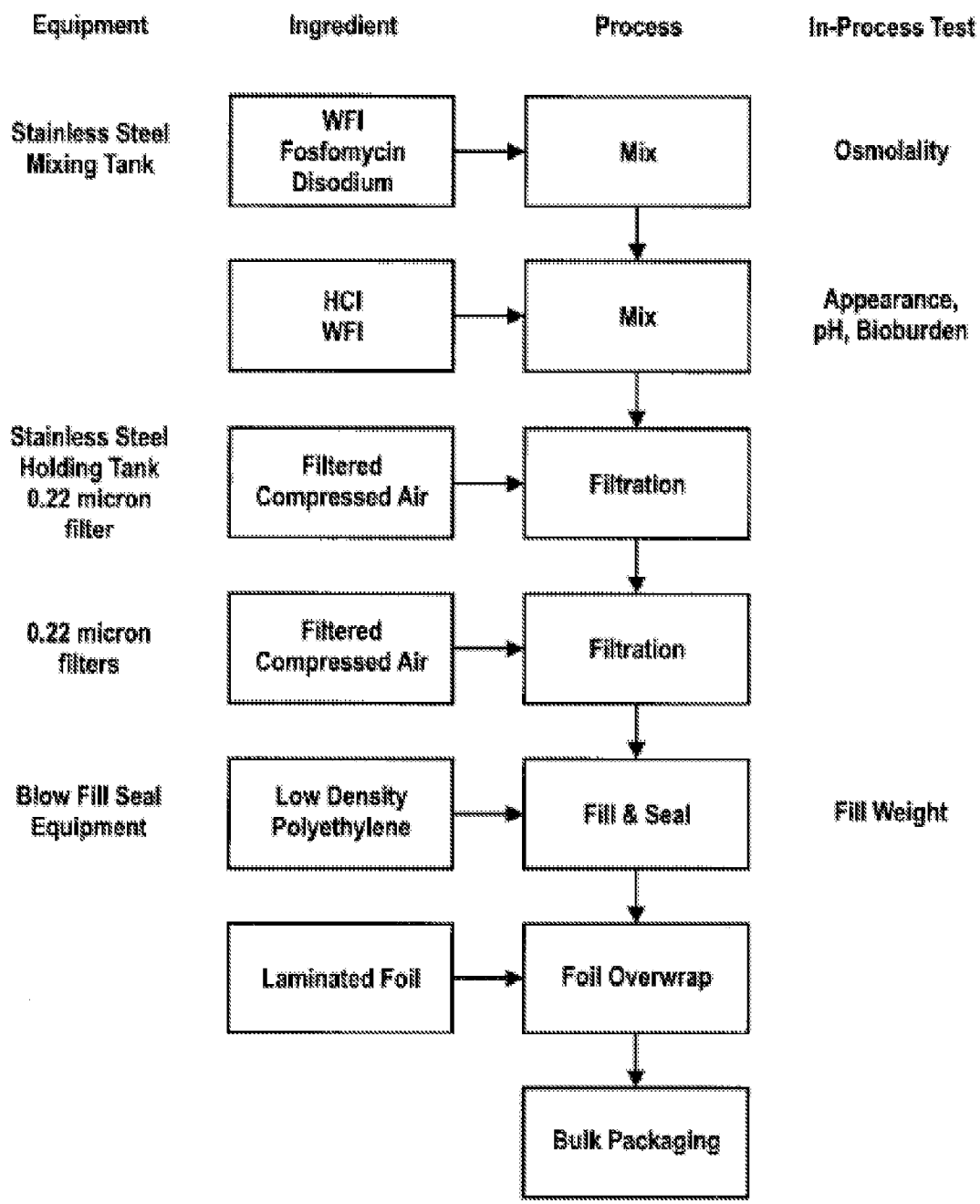
FIG. 2 is a flow diagram of the manufacturing steps of the fosfomycin disodium solution.

The flow diagram depicting the steps of the manufacturing process of fosfomycin solution is provided in FIG. 2. The flow diagram indicates where each raw material enters the manufacturing process. The manufacturing process is preferably conducted below 5° C.

The fosfomycin solution is manufactured as follows:
1. Add the calculated amount of WFI to the stainless steel tank.
2. Add the calculated amount of fosfomycin to the tank and mix until dissolved.
3. Add 90% of the calculated amount of HCl and mix for 5-10 minutes.
4. Titrate the solution with remaining HCl until solution reaches pH 8.0±0.3.
5. Bring the solution to final mass with WFI and mix for 10-15 minutes.
6. Filter the solution through a 0.22 micron filter into a holding tank.
7. Filter the solution through two 0.22 micro filters in series.
8. Use Blow/Fill/Seal equipment to form the LDPE ampoule; fill to a target weight; and then seal the ampoule.
9. Perform 100% visual inspection and integrity testing on LDPE ampoule.
10. Foil overwrap ampoules individually.
11. Perform 100% leak detection on foil overwrapped ampoules.
12. Maintain storage and transport at the less 5° C. to reduce impurities to less than 5% and preferably less than 3%.

EXAMPLE 4

Manufacturing and Packaging Process

Each solution is preferably contained in one overwrapped ampoule having dual chambers and a single opening for dispensing the combined solution into a nebulizer. In use, both solutions are aseptically combined for mixing in a single unit reservoir contained within the package to yield the pH balanced combination solution. A variety of known packaging options are available. For example, each sterile solution may be stored separately and combined upon removal of a barrier that is integral to the packaging and that allows sterile re-combination of the two solutions. Removal of this barrier may also open the reservoir of the package to allow dispensing the combined solution to the nebulizer.

EXAMPLE 5

Administration by Inline Nebulizer

An ideal aerosol delivery system for existing mechanical ventilators would have the following parameters: the system would be compatible with all ventilator models made of disposable components; capable of creating small particle aerosol size to prevent rain out in the endotracheal tube; and capable of rapid delivery of therapeutic quantities of antibiotic without creating additional airflow to trigger ventilator alarm or control systems. A nebulizer with these parameters, the PARI eFlow inline nebulizer, yields the data disclosed herein. By vibrating a laser-drilled, thin stainless steel membrane, a small nearly uniform particle aerosol is created for drug delivery. This technology has been proven in the handheld Altera® device recently approved to deliver aztreonam for inhalation in cystic fibrosis patients with chronic endobronchial *pseudomonas* infections. A similar membrane, modified by a smaller hole size and located in a unit that is placed inline with a ventilator inspiratory tubing is preferred. The design is unique with the membrane in the middle of the tubing, with the inspiratory flow freely moving around the membrane to entrain the aerosol as it is created. The nebulizer will be run continuously, and the estimated lung deposition is 15%. Bias flow, if a feature on the ventilator, will be adjusted to less than 5 liters/minute to prevent excess flushing of the drug during exhalation.

In practice, a patient is connected to a ventilator for breathing assistance and the ventilator system is adjusted to provide for a continuous and controlled airflow based on known physiological parameters. The antibiotic composition of the invention is introduced into a reservoir in the nebulizer and is stored therein until delivery. To administer the antibiotic combination of the present invention, the inline nebulizer is connected to the airway of the ventilator and activated to create the aerosol mist. Upon delivery, the nebulizer generates the aerosol mist from a vibrating apparatus disposed therein, typically a vibrating mesh or membrane that has numerous apertures formed therein to produce particles of a defined size from solution. The humidification generator is activated and maintained in operation during each delivery of the aerosol mist formed from the hypertonic solution such that the osmolar load is reduced. Thus, the advantage of an inline nebulizer as described herein is to permit the humidified air in the ventilation airway to pass through the nebulizer and to combine with the aerosolized portion of the hypertonic antibiotic combination solution All references cited herein are specifically incorporated by reference.

While the embodiments described herein are susceptible to various modifications and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

The invention claimed is:

1. A multi-component antibiotic pharmaceutical composition comprising: a bactericidal concentration of an aminoglycoside solution and a fosfomycin solution, each of which is sealed in a sterile container wherein the difference in pH of the two solutions is less than 2.0.

2. The composition of claim 1, wherein the pH of the aminoglycoside solution upon combinations yields a combined aminoglycoside / fosfomycin solution having a pH between 6.0 and 8.0.

3. The composition of claim 2, wherein the osmolality of the combined aminoglycoside / fosfomycin solution is less than about 1,000 mOsmol/L.

4. The composition of claim 1, wherein the concentration of the aminoglycoside is at least 50 mg/ml.

5. The composition of claim 1, wherein the concentration of fosfomycin is at least about 20 mg/ml.

6. The composition of claim 2, wherein the concentration of permeant anion in the combined aminoglycoside / fosfomycin solution is at least about 40 mEq/L and an osmolality is between about 310 mOsmol/L and less than about 800 mOsmol/L.

7. The composition of claim 1, wherein the fosfomycin solution contains between 100 and 300 mg fosfomycin.

8. The composition of claim 1, wherein the aminoglycoside solution is an amikacin chloride solution containing between 150 and 600 mg amikacin.

9. The composition of claim 1, wherein the fosfomycin solution has a pH between 7.5 and 8.5.

10. The composition of claim 8, wherein the amikacin chloride solution has a pH between 6.5 and 7.5.

11. The composition of claim 1, wherein each sterile container is combined into a single unit container comprising means for aseptically combining the two solutions.

12. The composition of claim 8, wherein the ratio of amikacin to fosfomycin is greater than 1:1.

13. A multi-component antibiotic composition comprising: a first component comprising an aminoglycoside solution having a first pH between about 6.5 and about 7.5; a second component comprising a fosfomycin solution having a second pH between about 7.5 and 8.5, and wherein the difference between the first pH and the second pH is less than 2.0.

14. The composition of claim 13, wherein the difference between the first pH and the second pH is less than 1.0.

15. The composition of claim 13, wherein a combination of the first component and the second component yield a combined solution of the first and second component having a pH between 6.9 and 7.4, at least 30 equil/L Chloride anion, and an osmolality between about 680 to 780 mOsmol/L.

16. The composition of claim 13, wherein the aminoglycoside is amikacin and the ratio of amikacin to fosfomycin is greater than 1:1.

17. The composition of claim 13, wherein the first component and the second component are sealed in separate containers as part of a single unit container further comprising means for aseptically combining the two components.

18. The composition of claim 13, wherein the aminoglycoside is amikacin solution containing approximately 100 mg/ml amikacin chloride.

19. The composition of claim 13, wherein the second component contains approximately 40 mg/ml fosfomycin.

20. A method to manufacture a multi-component antibiotic pharmaceutical composition comprising: formulating a bactericidal concentration of an aminoglycoside in a sterile solution in a first sealable container, and formulating a bactericidal concentration of a fosfomycin solution in a sterile solution in a second sealable container wherein the difference in pH of the solution in the first sealable container and the solution in the second sealable container is less than 2.0.

21. The method of claim 20, further comprising the step of combining the aminoglycoside solution and the fosfomycin solution to yield a combined solution having a pH between 6.0 and 8.0.

22. The method of claim 20, wherein the formulating steps are comprised of adjusting the osmolality of one or both of the solutions and wherein the aminoglycoside is amikacin at a concentration of at least 50 mg/ml.

23. The method of claim 20, wherein the concentration of fosfomycin is at least about 20 mg/ml.

24. The method of claim 20, wherein either or both formulating steps yield a concentration of permeant anion in the combined solution is at least about 40 mEq/L and an osmolality is between about 310 mOsmol/L and less than about 800 mOsmol/L.

25. The method of claim 20, wherein the step of formulating the fosfomycin solution yields a pH between 7.5 and 8.5.

26. The method of claim 20, wherein the step of formulating the aminoglycoside solution yields a pH between 6.5 and 7.5.

27. The method of claim 20, wherein the sterile container combines each separate sterile solution into a single unit container comprising means for aseptically combining the two solutions.

28. The method of claim 20, wherein the bactericidal concentration is a ratio of am ikacin to fosfomycin greater than 1:1.

29. A method to manufacture a multi-component antibiotic composition comprising: formulating a first component comprising an amikacin chloride solution having a concentration greater than 50 mg/ml and a first pH between about 6.5 and about 7.5 and formulating a second component comprising a fosfomycin solution having a concentration greater than 20 mg/ml and a second pH between about 7.5 and 8.5, and wherein the difference between the first pH and the second pH is less than 2.0.

30. The method of claim 29, wherein the formulating steps yield a difference between the first pH and the second pH of less than 1.0.

31. The method of claim 30, wherein the method further comprises mixing the amikacin chloride solution and the fosfomycin solution to yield a combined solution having a pH between 6.9 and 7.4, at least 30 equil/L Chloride anion and an osmolality between about 680 to 780 mOsmol/L.

32. The method of claim 30, wherein the ratio of concentration of amikacin to fosfomycin is greater than 1:1.

33. The method of claim 30, wherein the step of formulating the amikacin chloride solution is comprised of placing the amikacin chloride solution in a sterile, sealed container and the step of formulating the fosfomycin solution is comprised of placing the fosfomycin solution in a sterile, sealed container separate from the amikacin chloride solution, wherein the two sealed, separate containers are combined in a single unit container further comprising means for aseptically combining the two solutions.

* * * * *